United States Patent [19]
Ebel et al.

[11] Patent Number: 4,618,676
[45] Date of Patent: Oct. 21, 1986

[54] PREPARATION OF N,N',N''-TRIS(-2-HYDROXYPROPYL)-MELAMINE

[75] Inventors: Klaus Ebel, Ludwigshafen; Wolfgang Reuther, Heidelberg, both of Fed. Rep. of Germany

[73] Assignee: BASF Aktiengesellschaft, Ludwigshafen, Fed. Rep. of Germany

[21] Appl. No.: 787,087

[22] Filed: Oct. 15, 1985

[30] Foreign Application Priority Data

Oct. 19, 1984 [DE] Fed. Rep. of Germany ....... 3438387

[51] Int. Cl.$^4$ .......................................... C07D 251/70
[52] U.S. Cl. ................................................... 544/196
[58] Field of Search ......................................... 544/196

[56] References Cited

U.S. PATENT DOCUMENTS 4,312,988   1/1982   Jacobs et al. ...................... 544/196

OTHER PUBLICATIONS

Kaiser et al, Journal American Chemical Society, 73, 2985, (1951).

Primary Examiner—John M. Ford
Attorney, Agent, or Firm—Keil & Weinkauf

[57] ABSTRACT

N,N',N''-tris-(2-hydroxypropyl)-melamine is prepared by reacting melamine with isopropanolamine in the presence of an acidic catalyst, by a process in which the reaction is carried out at from 120° to 300° C. and using an excess of isopropanolamine, and the molar ratio of free isopropanolamine to the sum of free and converted melamine does not fall below 4:1 during the entire reaction time.

5 Claims, No Drawings

PREPARATION OF N,N'N''-TRIS-(2-HYDROXYPROPYL)-MELAMINE

The present invention relates to a novel process for the preparation of N,N',N''-tris-(2-hydroxypropyl)-melamine, by reacting melamine with an excess of isopropanolamine.

U.S. Pat. No. 4,312,988 discloses the reaction of melamine with ethanolamine or with isopropanolamine. In the said publication, it was found that, in the reaction of melamine with ethanolamine instead of N,N',N''-tris-(2-hydroxyethyl)-melamine, isomelamines were formed as the principal products in a repeating reaction with elimination of water, and are responsible for the low yield of N,N',N''-tris-(2-hydroxyethyl)-melamine. For example, in the reaction of ethanolamine with melamine in a molar ratio of 3.2:1, 20% of isomelamines were formed at 82% conversion, as much as 50% of isomelamines at 95% conversion and, finally, 100% of isomelamines at 99% conversion.

It was therefore proposed that isopropanolamine be used instead of ethanolamine. According to U.S. Pat. No. 4,312,988, it is supposed to be possible to reduce the formation of isomelamine dramatically by replacing the straight-chain ethanolamine with a branched isoalkanolamine.

However, the example described there, in which isopropanolamine and melamine are reacted in a molar ratio of 3.2:1, shows that the resulting end product still contains 40% of the undesirable isomelamines.

This proposal provides no hints regarding the preparation of N,N',N''-tris-(2-hydroxyethyl)-melamine which is virtually free of isomelamines, starting from melamine and isopropanolamine.

In fact, it has been possible to prepare pure, crystalline N,N',N''-tris-(2-hydroxypropyl)-melamine to date only by reacting the expensive compound cyanuric chloride with isopropanolamine; this reaction also produces a large amount of salt (J. Am. Chem. Soc. 73 (1951), 2985).

It is an object of the present invention to provide a process for the preparation of N,N',N''-tris-(2-hydroxypropyl)-melamine which uses melamine and isopropanolamine starting materials and in which the formation of isomelamine is prevented.

We have found that this object is achieved, and that N,N',N''-tris-(2-hydroxypropyl)-melamine can advantageously be prepared by reacting melamine with isopropanolamine in the presence of an acidic catalyst, if the reaction is carried out at from 120° to 300° C. and using an excess of isopropanolamine, and the molar ratio of free isopropanolamine to the sum of free and converted melamine does not fall below 4:1 during the entire reaction time.

N,N',N''-Tris-(2-hydroxypropyl)-melamine has the following structural formula:

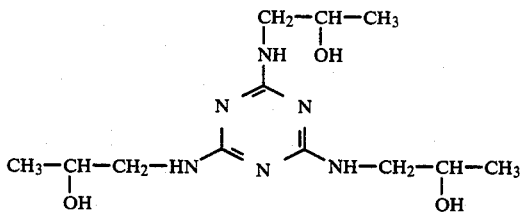

The novel process is advantageously carried out by initially taking a mixture of melamine, isopropanolamine, an acidic catalyst and, if required, a solvent, and heating the stirred mixture to 120°–300° C., in particular 150°–180° C.

The reaction is carried out in general under atmospheric pressure; however, in order to reach the upper temperature range (from 180° to 300° C.), a pressure of from 1 to 25 bar must be maintained.

It is also preferable to carry out the reaction in the presence of a protective gas, the latter generally being passed over the surface of the reaction mixture. Examples of suitable protective gases are noble gases and, in particular, nitrogen.

Suitable acidic catalysts are all strong and moderately strong acids, e.g. hydrofluoric acid, hydrochloric acid, hydrobromic acid, sulfuric acid, nitric acid, phosphoric acid, amidosulfonic acid, thiocyanic acid, p-toluenesulfonic acid and methanesulfonic acid.

The acids can be added either in the free form or as a melamine or isopropanolamine salt. They may also be added in the form of a salt of a base which is weaker than isopropanolamine, for example in the form of an ammonium salt.

Instead of the stated protic acids, it is also possible to catalyze the reaction with a Lewis acid, such as boron trifluoride, aluminum chloride, zinc(IV) chloride, antimony(V) fluoride or iron(II) bromide.

From 0.05 to 3 moles, preferably from 0.1 to 1 mole, of catalyst are employed per mole of melamine. Where the protic acid is used in the form of its melamine salt, the amount of melamine from the salt must be taken into account. The molar ratio of free isopropanolamine to the sum of free and converted melamine must not fall below the required value of 4:1. The reaction rate is found to increase as the amount of catalyst increases.

The novel process is preferably carried out in the presence of an organic solvent, although the latter may also be absent.

Suitable organic solvents are polyols, e.g. ethylene glycol, 1,2-propylene glycol, diethylene glycol or triethylene glycol. Ethylene glycol is preferably used.

The molar ratio of free isopropanolamine to the sum of free and converted melamine is a critical process parameter and must not fall below 4:1 during the entire reaction time. Converted melamine is considered to be N,N',N''-tris-(2-hydroxypropyl)-amine and, where they are present, its intermediates N-mono-(2-hydroxypropyl)-melamine and N,N',N''-bis-(2-hydroxypropyl)-melamine.

In a preferred embodiment of the novel process, the molar ratio of free isopropanolamine to the sum of free and converted melamine is kept at from 5:1 to 12:1 during the entire reaction time. The use of a molar ratio >15:1 has no further advantages since in this case the reaction time is increased considerably.

To isolate the desired product, the particular catalyst acid is neutralized by adding a base, e.g. sodium hydroxide, potassium hydroxide, sodium carbonate, potassium carbonate, calcium carbonate or barium carbonate. Excess isopropanolamine and any organic solvent used are then distilled off under reduced pressure (about 30 mbar) at from 150° to 200° C., and water is added to the resulting residue.

This results in the formation of two phases, an organic phase and an aqueous phase, which contains the salts. The organic phase is separated off, and water is added to it again. When the solution is cooled, pure N,N',N''-tris-(2-hydroxypropyl)-melamine then crystallizes out in the form of colorless crystals, which are isolated and dried.

The novel process gives virtually isomelamine-free N,N',N''-tris-(2-hydroxypropyl)-melamine, thus ensuring that its full NH and OH functionality is retained. The end product is obtained in high purity and good yield.

N,N',N''-Tris-(2-hydroxypropyl)-melamine is a useful intermediate, for example for the preparation of urethanes.

The Examples which follow illustrate the invention.

EXAMPLES 1 TO 6

Examples 1 to 6 were carried out under the same reaction conditions, the only difference being the excess amount of isopropanolamine used. The acidic catalyst used in each case was ammonium chloride.

Procedure for Examples 1 to 6

Melamine, the catalyst, isopropanolamine and ethylene glycol as a solvent were stirred under reflux in an oil bath at 200° C., while a gentle stream of nitrogen was passed over the mixture. The reaction was monitored by taking samples and subjecting them to high pressure liquid chromatography (HPLC).

The weights of the starting materials and the HPLC evaluation are shown in the Table below. A comparison was made between the amounts of by-product obtained for the largest amount of N,N',N''-tris-(2-hydroxypropyl)-melamine in each case. The way in which the amount of by-product decreases as the excess of isopropanolamine increases is clearly recognizable.

Only in Example 6 (molar ratio of isopropanolamine to melamine 1:15) was the reaction terminated prematurely, this being done because of the extremely long reaction time of more than 50 hours.

320 g (4 moles) of 50% strength by weight sodium hydroxide solution. Excess isopropanolamine and ethylene glycol were then distilled off under 30 mbar and at a bottom temperature of not more than 200° C.

800 g of warm water were added to the residue, resulting in the formation of two phases. The aqueous phase was separated off, and a further 200 ml of water were added to the organic phase, a homogeneous solution being formed. When the solution was cooled, N,N',N''-tris-(2-hydroxypropyl)-melamine crystallized out and was filtered off under suction and dried. 850 g (71%) of colorless crystals of melting point 131° C. were obtained.

When the mother liquor was evaporated down to about one third of its original volume, a further 197 g (17%) of N,N',N''-tris-(2-hydroxypropyl)-melamine of melting point 126° C. were obtained.

According to HPLC analysis, the N,N',N''-tris-(2-hydroxypropyl)-melamine obtained was identical to a comparative sample prepared from cyanuric chloride and isopropanolamine and had a purity of 99%. Spectroscopic data ($^1$H-NMR spectrum, IR spectrum and mass spectrum) also confirm the structure.

We claim:

1. In a process for the preparation of N,N',N''-tris-(2-hydroxypropyl)-melamine by reacting melamine with isopropanolamine in the presence of an acidic catalyst and at a temperature of from 120° to 300° C., the improvement which comprises: maintaining the molar ratio of free isopropanolamine to the sum of free and converted melamine at a level of at least 4:1 during the entire reaction time.

2. The process of claim 1, wherein the reaction is carried out at from 150° to 180° C. and under atmospheric pressure.

3. The process of claim 1, wherein the reaction is carried out in the presence of an organic solvent.

TABLE

|  | Example 1 | | Example 2 | | Example 3 | | Example 4 | | Example 5 | | Example 6 | |
| --- | --- | --- | --- | --- | --- | --- | --- | --- | --- | --- | --- | --- |
|  | Weight of starting material (g) | Molar ratio | Weight of starting material (g) | Molar ratio | Weight of starting material (g) | Molar ratio | Weight of starting material (g) | Molar ratio | Weight of starting material (g) | Molar ratio | Weight of starting material (g) | Molar ratio |
| Melamine | 31.5 | 1 | 31.5 | 1 | 31.5 | 1 | 31.5 | 1 | 25.2 | 1 | 18 | 1 |
| Ethylene glycol | 31.0 | 2 | 31.0 | 2 | 46.5 | 3 | 46.5 | 3 | 24.8 | 2 | 17.7 | 2 |
| Ammonium chloride | 13.4 | 1 | 13.4 | 1 | 13.4 | 1 | 13.4 | 1 | 10.7 | 1 | 7.6 | 1 |
| Isopropanolamine | 93.8 | 5 | 112.5 | 6 | 131.3 | 7 | 150.0 | 8 | 150.0 | 10 | 160.7 | 15 |
|  | HPLC evaluation [% by area] | | HPLC evaluation [% by area] | | HPLC evaluation [% by area] | | HPLC evaluation [% by area] | | HPLC evaluation [% by area] | | HPLC evaluation [% by area] | |
| Bis-HPM* | 3 | | 2 | | 2 | | 6 | | 4 | | 16 | |
| Tris-HPM** | 32 | | 57 | | 71 | | 79 | | 83 | | 80 | |
| By-products | 65 | | 41 | | 27 | | 15 | | 11 | | 5 | |

*Bis-HPM = N,N'—bis-(2-hydroxypropyl)-melamine
**Tris-HPM = N,N',N''—tris-(2-hydroxypropyl)-melamine

EXAMPLE 7

A mixture of 504 g (4 moles) of melamine, 214 g (4 moles) of ammonium chloride and 2400 g (32 moles) of isopropanolamine in 496 g (8 moles) of ethylene glycol was stirred under reflux at from 162° to 178° C. for 63 hours, a gentle stream of nitrogen being passed over the surface of the reaction mixture. Thereafter, the reaction mixture was cooled to 90° C. and neutralized by adding 4. The process of claim 1, wherein the reaction is carried out in the presence of ethylene glycol as the organic solvent.

5. The process of claim 1, wherein the molar ratio of free isopropanolamine to the sum of free and converted melamine is maintained at from 5:1 to 12:1 during the entire reaction time.